United States Patent [19]

Stadler et al.

[11] 4,350,634
[45] Sep. 21, 1982

[54] N-BENZOYL-N'-3-INDOLYL-N'ALKYL-1,3-DIAMINOPROPANES

[75] Inventors: Paul Stadler, Biel-Benken; Franz Troxler, Bottmingen, both of Switzerland

[73] Assignee: Sandoz Ltd., Basel, Switzerland

[21] Appl. No.: 111,445

[22] Filed: Jan. 11, 1980

Related U.S. Application Data

[63] Continuation-in-part of Ser. No. 922,520, Jul. 7, 1978, abandoned.

[30] Foreign Application Priority Data

| Jul. 12, 1977 | [CH] | Switzerland | 8583/77 |
| Jul. 12, 1977 | [CH] | Switzerland | 8584/77 |
| Jul. 12, 1977 | [CH] | Switzerland | 8585/77 |
| Jul. 12, 1977 | [CH] | Switzerland | 8586/77 |
| Jul. 12, 1977 | [CH] | Switzerland | 8587/77 |
| Jul. 12, 1977 | [CH] | Switzerland | 8588/77 |
| Jul. 12, 1977 | [CH] | Switzerland | 8589/77 |
| Mar. 20, 1978 | [CH] | Switzerland | 3008/78 |

[51] Int. Cl.³ .................. C07D 209/12; A61K 31/40
[52] U.S. Cl. .................. 260/326.13 B; 260/326.13 H; 260/326.12 R; 260/326.15; 546/65; 546/193; 546/201; 424/274; 424/275; 424/267; 424/263
[58] Field of Search .................. 260/326.13 B

[56] References Cited
FOREIGN PATENT DOCUMENTS
839347  3/1975  Belgium .

OTHER PUBLICATIONS

De Groot et al, J. Org. Chem., 31, p. 3954 (1966).
Archibald et al, J. Med. Chem., vol. 14, No. 11, p. 1054 (1971).

*Primary Examiner*—David B. Springer
*Attorney, Agent, or Firm*—Gerald D. Sharkin; Robert S. Honor

[57] ABSTRACT

The invention provides indole compounds useful for the treatment of hypertension, processes for the preparation of said compounds and pharmaceutical compositions containing these compounds.

The compounds of the invention have the formula

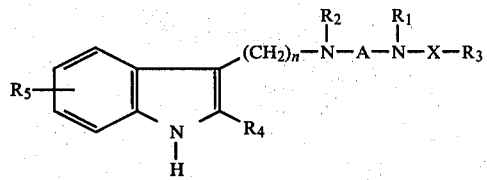

wherein n is 2 or 3, A is 1,4-cyclohexylidene or trimethylene and $R_1$ is H or alkyl, or A together with $NR_1$ is 4-piperidyl, $R_2$ is hydrogen or alkyl, $R_3$ is alkyl, cycloalkyl, amino, alkylamino, dialkylamino, phenylamino, unsubstituted or substituted phenyl or benzyl, pyridylmethyl or an heterocycle, $R_4$ is hydrogen, chlorine, bromine or alkyl, $R_5$ is hydrogen, alkyl, alkoxy or alkylthio, and X is —CO— or —CS.

5 Claims, No Drawings

N-BENZOYL-N'-3-INDOLYL-N'ALKYL-1,3-DIAMINOPROPANES

This application is a continuation in part of my application Ser. No. 922,520 filed July 7, 1978, abandoned.

The present invention relates to new indole derivates, processes for their preparation, and pharmaceutical compositions containing them.

In accordance with the invention there are provided new compounds of formula I

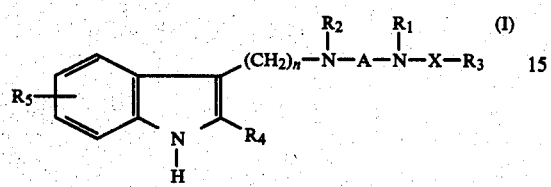

wherein n is 2 or 3,
either A is trimethylene optionally substituted by $(C_{1-4})$ alkyl or 1,4-cyclohexylidene and $R_1$ is hydrogen or $(C_{1-5})$ alkyl, or A together with $R_1$ and the nitrogen atom to which $R_1$ is bound, form a 4-piperidyl radical, $R_2$ is hydrogen or $(C_{1-5})$ alkyl, $R_3$ is $(C_{1-4})$ alkyl; $(C_{3-6})$cycloalkyl; amino; $(C_{1-4})$alkylamino; di$(C_{1-4})$alkylamino; phenylamino wherein the phenyl ring is unsubstituted or mono-, di- or trisubstituted independently by halogen, $(C_{1-4})$alkyl, $(C_{1-4})$alkoxy or di$(C_{1-4})$alkylamino; phenyl or benzyl wherein the phenyl rings are unsubstituted or mono-, di- or trisubstituted independently by halogen, hydroxy, $(C_{1-4})$alkyl, $(C_{1-4})$alkoxy or di-$(C_{1-4})$alkylamino; 2-, 3- or 4-pyridylmethyl; or an aromatic 5- or 6-membered heterocycle containing one heteroatom chosen from nitrogen, oxygen or sulphur and optionally additional one or two nitrogen atoms, $R_4$ is hydrogen, chlorine, bromine or $(C_{1-4})$alkyl, $R_5$ is hydrogen, $(C_{1-4})$alkyl, $(C_{1-4})$alkoxy or $(C_{1-4})$alkylthio, and X is —CO— or —CS—.

Any alkyl, alkoxy or alkylthio radical contains preferably two carbon atoms, especially one carbon atom. Halogen means fluorine, chlorine, bromine or iodine, especially chlorine.

When A is 1,4-cyclohexylidene, this may be cis or trans-1,4-cyclohexylidene.

When A is optionally substituted trimethylene, this is preferably either unsubstituted or monosubstituted, conveniently at the middle carbon atom.

When $R_1$ and $R_2$ are chosen from hydrogen or alkyl, these are preferably alkyl.

Conveniently A is optionally substituted trimethylene or 1,4-cyclohexylidene. Preferably A is optionally substituted trimethylene.

When $R_3$ is or contains a dialkylamino radical, the alkyl groups are preferably the same. When $R_3$ is an optionally substituted phenyl or phenylamino radical, the substituents are conveniently identical. Conveniently these radicals are unsubstituted or monosubstituted preferably in the para position. When $R_3$ is a heterocycle, conveniently this contains one heteroatom chosen from nitrogen, oxygen or sulphur and optionally a second nitrogen atom, e.g. thienyl, furyl, pyrrolyl, pyridyl or pyrazinyl. Conveniently the heterocycle is bound to X by a ring carbon atom adjacent to a heteroatom.

$R_3$ is preferably unsubstituted phenyl.

$R_4$ and $R_5$ are conveniently hydrogen. X is conveniently —CO—.

The present invention provides a process for the production of a compound of formula I as defined above, which comprises
acylating a compound of formula II

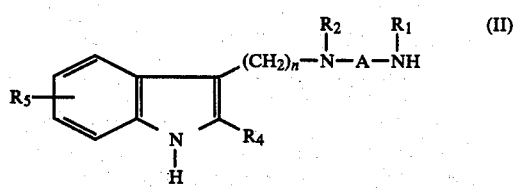

wherein n, A and $R_1$ to $R_5$ are as defined above, or
(b) condensing a compound of formula III

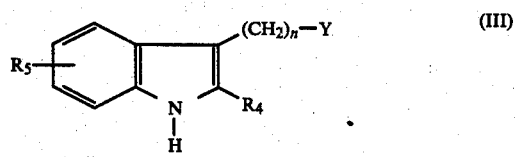

wherein n, $R_4$ and $R_5$ are as defined above, and Y is a leaving group, with a compound of formula IV

wherein A, $R_1$ to $R_3$ and X are as defined above.

Process (a) may be effected in conventional manner for the production of amides or thio-amides from amines. For example there may be used, as acylating agent, a compound of formula V $$Z-X-R_3' \qquad (V)$$

wherein X is as defined above, $R_3'$ has the same signification as $R_3$ but is other than amino, alkylamino and optionally substituted phenylamino and Z is chlorine or bromine. The reaction may be effected conveniently in a solvent such as pyridine and at temperatures from 0° to 25°. Alternatively when $R_3$ is amino, alkylamino or optionally substituted phenylamino, there may be used a compound of formula VI $$X=R_6 \qquad (VI)$$

wherein X is as defined above and $R_6$ is imino, alkylimino or optionally substituted phenylimino. The reaction may be effected conveniently in a solvent such as dimethylformamide and at temperatures from 5° to 25°. A compound of formula VI wherein $R_6$ is imino may be prepared in situ from potassium or sodium cyanate or thiocyanate, by treatment with acid, for example hydrochloric acid.

Process (b) may be effected in conventional manner for a condensation reaction to produce a secondary or tertiary amine. Y is conveniently chlorine, bromine, iodine, tosyloxy or mesyloxy. The reaction may be conveniently effected in acetone or dimethylformamide. Suitable reaction temperatures are from 20° to 150°.

The compounds of formula I may be isolated from the reaction mixture and purified in known manner. The free base forms may be converted into acid addition salt forms in the usual manner and vice versa. Suitable acids for salt formation are hydrochloric acid, oxalic acid, fumaric acid, naphthalene-2-sulphonic acid and naphthalene-1,5-disulphonic acid.

The starting material of formula II may be produced from a compound of formula III and a compound of formula VII

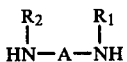
(VII)

wherein A, $R_1$ and $R_2$ are as defined above, in analogous manner to process (b).

When the amine of formula VII is unsymmetrical, the conditions should be chosen to avoid the formation of the undesired corresponding compound produced by condensation at the nitrogen atom bearing the $R_1$ substituent. For this purpose the amine may be used in protected form of formula VIII

(VIII)

wherein $R_7$ is a protecting group, such as benzyl or benzyloxy, which may be removed from the resulting product, e.g. by hydrogenolysis.

A starting material of formula IIa

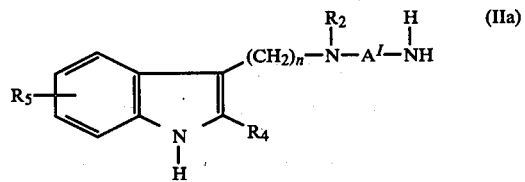
(IIa)

wherein $A^I$ is

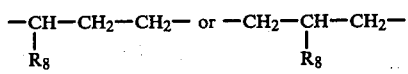

and wherein $R_8$ is $(C_{1-4})$alkyl and n, $R_2$, $R_4$ and $R_5$ are as defined above, may alternatively be produced by reducing a compound of formula IX

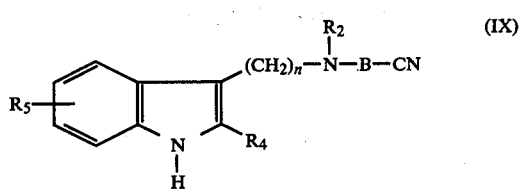
(IX)

wherein B is $-CH(R_8)-CH_2-$ or $-CH_2-CH(R_8)-$ and n, $R_2$, $R_4$, $R_5$ and $R_8$ are as defined above, e.g. by hydrogenation in the presence of Raney-nickel.

Any starting material of formula II wherein $R_1$ and/or $R_2$ is hydrogen may be converted into a corresponding compound wherein $R_1$ and $R_2$ are both alkyl, or $R_1$ is alkyl and $R_2$ is hydrogen under appropriate selective alkylation conditions.

The starting material of formula IV may be produced by acylating an amine of formula VII in analogous manner to process (a). If desired, one nitrogen atom of an unsymmetrical amine may be protected to facilitate production of the desired product.

A starting material of formula IVa

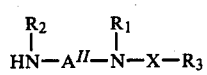
(IVa)

wherein X, $R_2$ and $R_3$ are as defined above and $A^{II}$ together with $R_1$ and the nitrogen atom to which $R_1$ is bound, form a 4-piperidyl radical, may alternatively be produced by acylating 4-piperidone with a compound of formula V or VI and condensing the resulting compound of formula X

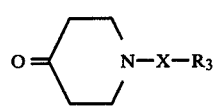
(X)

wherein X and $R_3$ are as defined above, with a compound of formula XI

 (XI)

wherein $R_2$ is as defined above, under simultaneous reduction, e.g. with hydrogen in presence of a catalyst.

Insofar as the production of any starting material is not particularly described, these are known or may be produced in conventional manner or in a manner analogous to that described above.

In the following non-limitative Examples all temperatures are indicated in degrees Centigrade.

EXAMPLE 1

N-benzoyl-N'-[3-(3-indolyl)propyl]-N'-methyl-1,3-diaminopropane

A solution of 10.1 g benzoyl chloride in 15 ml anhydrous methylene chloride is added dropwise with stirring for 25 minutes between 0° and 10° to a solution of 14.5 g N-[3-(3-indolyl)propyl]-N-methyl-1,3-diaminopropane in 150 ml anhydrous pyridine and the reddish clear solution is stirred for 2 hours at 0°. The reaction mixture is divided between a 2 N sodium carbonate solution and methylene chloride, and the organic phase is washed, dried and evaporated. Chromatographic purification of the resinous product on aluminium oxide using methylene chloride with 0.1 to 0.3% of methanol yields the title compound. The naphthalene-2-sulfonate-dihydrate, obtained by conventional methods, melts at 73°–74° after crystallization from methanol/water-/ethyl acetate (1:1:1).

The starting material may be obtained as follows:

(a) A mixture of 57 g trifluoroacetic acid and 105 g trifluoroacetic anhydride in 400 ml anhydrous acetonitrile are added dropwise to a stirred suspension of 95.1 g 3-(3-indolyl)propionic acid in 500 ml anhydrous acetonitrile and maintained with stirring at −15° for 30 minutes. Under good cooling 500 ml anhydrous pyridine are added between −20° and −15° and quickly 238 ml of a 4.2 N solution of anhydrous methylamine in acetonitrile. The mixture is warmed with stirring at 0° for 15 minutes and maintained to 0° for 3 hours. 3-(3-indolyl)-N-methyl-propionamide (M.pt 97°–98° after crystallization from methylene chloride/ethyl acetate) is obtained after working up.

(b) A solution of 60.6 g 3-(3-indolyl)-N-methyl-propionamide in 500 ml anhydrous tetrahydrofuran are added dropwise at 25° for 15 minutes under nitrogen atmosphere to a suspension of 34.2 g lithium aluminium hydride in 800 ml anhydrous tetrahydrofuran and maintained at 66° for 3 hours. N-methyl-3-(3-indolyl)-propylamine (M.pt 81°–82° after crystallization from methylene chloride/ethyl acetate) is obtained after working up.

(c) A mixture of 37.6 g N-methyl-3-(3-indolyl)-propylamine and 21, 2 g acrylonitrile in 65 ml anhydrous 1,2-dimethoxyethane are warmed with stirring at 60°0 for 2½ hours. N-(2-cyanoethyl-N-methyl-3-(3-indolyl)propylamine (M.pt 48°–49° after crystallization from isopropyl ether) is obtained after working up.

(d) 36.2 g N-(2-cyanoethyl)-N-methyl-3-(3-indolyl)-propyl amine are hydrogenated at normal pressure and at room temperature with 20 g Raney-nickel catalyst in 400 ml dioxan and 400 ml of a 10% ammonia solution. N-[3-(3-indolyl)propyl]-N-methyl-1,3-diaminopropane is obtained after working up. M.pt of the neutral fumarate: 180°–181° (with decomposition) after crystallization from ethanol.

From the appropriate compounds of formula II the following compounds of formula I wherein X is —CO— may be obtained in analogous manner to Example 1.

| Ex. | n | $R_1$ | A | $R_2$ | $R_3$ | $R_4$ | $R_5$ | M.Pt. |
|---|---|---|---|---|---|---|---|---|
| (a) | 2 | H | —(CH$_2$)$_3$— | —CH$_3$ | phenyl | H | H | 122–24°[(1)(10)] |
| (b) | 2 | H | —(CH$_2$)$_3$— | —CH$_3$ | phenyl | H | 4-OC$_2$H$_5$ | 189–190°[(9)(10)] |
| (c) | 3 | H | —(CH$_2$)$_3$— | —CH$_3$ | phenyl | —CH$_3$ | H | |
| (d) | 3 | H | —(CH$_2$)$_3$— | —CH$_3$ | phenyl | H | 6-SCH$_3$ | |
| (e) | 3 | H | —(CH$_2$)$_3$— | —CH$_3$ | phenyl | H | 5-OCH$_3$ | |
| (f) | 3 | H | —(CH$_2$)$_3$— | —CH$_3$ | phenyl | H | 4-OCH$_3$ | |
| (g) | 3 | H | —(CH$_2$)$_3$— | —C$_2$H$_5$ | phenyl | H | H | amorphous[(6)] |
| (h) | 3 | —CH$_3$ | —(CH$_2$)$_3$— | —CH$_3$ | phenyl | H | H | 124–126°[(1)] |
| (i) | 3 | —n-C$_3$H$_7$ | —(CH$_2$)$_3$— | —CH$_3$ | phenyl | H | H | 82–84°[(1)(7)] |
| (j) | 3 | H | —(CH$_2$)$_3$— | —CH$_3$ | benzyl | H | H | amorphous[(8)] |
| (k) | 2 | H | cyclohexylidene (H,H) | —CH$_3$ | phenyl | H | H | 173–175°[(2)(10)] |
| (l) | 2 | H | cyclohexylidene (H,H) | —CH$_3$ | phenyl | H | H | 133–134° |
| (m) | 3 | H | —(CH$_2$)$_3$— | —CH$_3$ | 3,4,5-tri-methoxybenzyl | H | H | 77–80°[(2)] |
| (n) | 3 | H | —(CH$_2$)$_3$— | —CH$_3$ | o-chlorophenyl | H | H | amorphous[(6)] |
| (o) | 2 | H | —(CH$_2$)$_3$— | H | diethylamino | H | H | 191–192°[(3)] |
| (p) | 2 | H | —(CH$_2$)$_3$— | —CH$_3$ | dimethylamino | H | H | 85–87° |
| (q) | 2 | H | —(CH$_2$)$_3$— | —CH$_3$ | p-methoxyphenyl | H | H | 133–135°[(2)(10)] |
| (r) | 3 | H | —(CH$_2$)$_3$— | —CH$_3$ | p-dimethylaminophenyl | H | H | 107–108° |
| (s) | 3 | H | —(CH$_2$)$_3$— | —CH$_3$ | m-tolyl | H | H | amorphous[(6)] |
| (t) | 2 | H | —(CH$_2$)$_3$— | —n-C$_3$H$_7$ | p-tolyl | H | H | 181–183°[(2)(10)] |
| (u) | 3 | H | —(CH$_2$)$_3$— | —CH$_3$ | m-chlorophenyl | H | H | 133–134°[(1)] |
| (v) | 2 | H | —(CH$_2$)$_3$— | —CH$_3$ | p-chlorophenyl | H | H | 161–163°[(2)(10)] |
| (w) | 3 | H | —(CH$_2$)$_3$— | —CH$_3$ | 3,5-dimethoxyphenyl | H | H | 137–138°[(2)(10)] |
| (x) | 3 | H | —(CH$_2$)$_3$— | —CH$_3$ | 3,4,5-trimethoxyphenyl | H | H | 103–105°[(2)(10)] |
| (y) | 3 | H | —(CH$_2$)$_3$— | —CH$_3$ | o-methoxyphenyl | H | H | amorphous[(6)] |
| (z) | 2 | H | —(CH$_2$)$_3$— | —CH$_3$ | 2-furyl | H | H | 95–96° |
| (aa) | 3 | H | —(CH$_2$)$_3$— | —CH$_3$ | 2-furyl | H | H | 80–82°[(1)] |
| (ab) | 3 | H | —(CH$_2$)$_3$— | —CH$_3$ | 2-thienyl | H | H | 82–84°[(1)(7)] |
| (ac) | 3 | H | —(CH$_2$)$_3$— | —CH$_3$ | 2-pyridyl | H | H | 122–124°[(5)(10)] |
| (ad) | 3 | H | —(CH$_2$)$_3$— | —CH$_3$ | 3-pyridyl | H | H | |
| (ae) | 3 | H | —(CH$_2$)$_3$— | —CH$_3$ | 4-pyridyl | H | H | 118–121°[(4)(10)] |
| (af) | 3 | H | —(CH$_2$)$_3$— | —CH$_3$ | pyrazinyl | H | H | 174–175°[(9)(10)] |
| (ag) | 3 | H | —(CH$_2$)$_3$— | —CH$_3$ | 2-pyridylmethyl | H | H | amorphous |
| (ah) | 3 | H | —(CH$_2$)$_3$— | —CH$_3$ | 2-pyrrolyl | H | H | 89–91°[(1)(7)] |
| (ai) | 2 | —CH$_3$ | —CH$_2$—CH(CH$_3$)—CH$_2$— | —CH$_3$ | phenyl | H | H | 114–115°[(11)] |
| (aj) | 2 | H | —(CH$_2$)$_3$— | —CH$_3$ | 4-hydroxyphenyl | H | H | |
| (ak) | 3 | H | —(CH$_2$)$_3$— | —CH$_3$ | 4-hydroxyphenyl | H | H | |
| (al) | 3 | H | —(CH$_2$)$_3$— | —CH$_3$ | phenyl | H | 6-CH$_3$ | |
| (am) | 3 | H | —(CH$_2$)$_3$— | —CH$_3$ | phenyl | H | 5-CH$_3$ | 148–149°[(9)(10)] |
| (an) | 3 | H | —(CH$_2$)$_3$— | —CH$_3$ | phenyl | H | 4-CH$_3$ | |

-continued

| Ex. | n | $R_1$ | A | $R_2$ | $R_3$ | $R_4$ | $R_5$ | M.Pt. |
|---|---|---|---|---|---|---|---|---|
| (ao) | 3 | H | $-(CH_2)_3-$ | $-C_2H_5$ | phenyl | H | H | |

(1) naphthalene-2-sulfonate
(2) hydrogen oxalate
(3) bis[base]naphthalene-1,5-disulfonate
(4) dihydrobromide
(5) dihydrochloride ½ $H_2O$
(6) dihydrogen phosphate
(7) monohydrate
(8) bis[base]sulphate
(9) bis[base]fumarate
(10) with decomposition
(11) hydrogen fumarate

EXAMPLE 2

N-phenylcarbamoyl-N'-[2-(3-indolyl)ethyl]-N'-methyl-1,3-diaminopropane 3 ml phenyl isocyanate are added dropwise between 5° and 10° and with stirring to a solution of 5.8 g N-[2-(3-indolyl)ethyl]-N-methyl-1,3-diaminopropane in 25 ml anhydrous dimethylformamide. The solution is stirred for an hour between 10° and 15° and evaporated. The residue is dried in high vacuum and chromatographed on silicagel using methylene chloride with 6 to 10% methanol, to yield the title compound (M.pt. of the hydrogen maleate 153°–155° with decomposition after crystallization from alcohol/acetone).

The starting material may be obtained as follows:

(a) Reaction of 3-[2-methylamino)ethyl]indole with acrylonitrile in dimethoxy-ethane yields the N-(2-cyanoethyl)-N-methyl-2-(3-indolyl)ethylamine which is worked up further directly.

(b) Reduction of N-(2-cyanoethyl)-N-methyl-2-(3-indolyl)-ethylamine with Raney-Nickel catalyst yields the N-[2-(3-indolyl)ethyl]-N-methyl-1,3-diaminopropane (M.pt. of the fumarate 153°–154°).

EXAMPLE 3

N-Benzoyl-N'-[2-(3-indolyl)ethyl]-1,3-diaminopropane

A solution of 8 g N-benzoyl-1,3-diaminopropane, 6,7 g 3-(2-bromoethyl)indole and 5 ml anhydrous triethylamine in 15 ml anhydrous dimethylformamide is maintained for 72 hours in nitrogen atmosphere. A dilute ammonia solution and methylene chloride are then added to the reaction mixture and the organic phase is dried and evaporated. The residue is chromatographied on silicagel using as eluant methylene chloride+5% methanol+0.3% ammonia, to yield the title compound (M.pt. of the naphthalene-2-sulfonate 203°–204° with decomposition after crystallization from ethanol).

The following compounds of formula may be obtained in analogous manner to Example 3:

TABLE

| Ex. No. | $R_2$ | $R_3$ | $R_4$ | M.Pt. |
|---|---|---|---|---|
| (a) | $-n-C_3H_7$ | p-tolyl | H | 181–183°(1)(3) |
| (b) | $-CH_3$ | p-methoxyphenyl | H | 133–135°(1)(3) |
| (c) | $-CH_3$ | p-chlorophenyl | H | 161–163°(1)(3) |
| (d) | $-CH_3$ | phenyl | H | 122–124°(2)(3) |
| (e) | $-CH_3$ | 2-furyl | H | 95–96° |
| (f) | $-CH_3$ | phenyl | Br | 148–150°(1)(3) |

(1) hydrogen oxalate
(2) naphthalene-2-sulfonate
(3) with decomposition

EXAMPLE 4

From the appropriate 4-amino-piperidines and 2-(3-indolyl)ethyl bromide or 3-(3-indolyl)propyl bromide, the following compounds of formula may be obtained in analogous manner to Example 3:

TABLE

| Ex. No. | n | $R_2$ | $R_3$ | M.Pt. |
|---|---|---|---|---|
| (a) | 2 | $-CH_3$ | phenyl | 131–133°(3) |
| (b) | 3 | $-CH_3$ | phenyl | 201–203°(1)(3) |
| (c) | 2 | iso-$C_4H_9$ | phenyl | 152–154°(2)(3) |
| (d) | 2 | H | phenyl | 151–152°(3) |
| (e) | 2 | $-CH_3$ | phenylamino | 58–60° |
| (f) | 2 | H | dimethylamino | 119–120° |

(1) naphthalene-2-sulfonate
(2) hydrochloride
(3) with decomposition

In analogous manner to Example 1 there may be produced compounds of formula I wherein n is 3, A is trimethylene, $R_1$ and $R_2$ are n-butyl, $R_4$ is chlorine, $R_5$ 7-ethyl, X is $-CS-$ and $R_3$ is

| | |
|---|---|
| n-$C_3H_7$ | (a) |
| cyclopropyl | (b) |
| cycloheptyl | (c) |
| ethylamino | (d) |

(e)

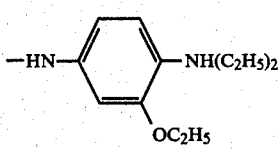 (f)

The compounds of formula I are useful because they possess pharmacological activity in animals. In particular, the compounds are useful as anti-hypertensive agents, as indicated by standard tests, e.g. in the awake renal hypertonic Grollman rat, upon administration of 1 to 50 mg/kg animal body weight of the compounds and in the awake renal hypertonic Goldblatt dog, upon administration of 1 to 10 mg/kg animal body weight of the compounds.

For the above-mentioned use, the dosage administered will, of course, vary depending on the compound employed, mode of administration and treatment desired. However, in general satisfactory results are obtained when administered at a daily dosage of from about 0.1 to 100 mg/kg animal body weight, conveniently given in divided doses 2 to 3 times a day or in sustained release form. For the larger mammals, the total daily dosage is in the range of from about 10 to 2000 mg, and dosage forms suitable for oral administration comprise from about 2,5 to 1000 mg of the compound admixed with a solid or liquid pharmaceutical carrier or diluent.

A particularly interesting compound is the Example 1 compound.

The compounds of formula I may be administered in pharmaceutically acceptable acid addition salt form. Such salts process the same order of activity as the free base forms.

The invention also provides a pharmaceutical composition comprising a compound of formula I, in free base or pharmaceutically acceptable acid addition salt form, in association with a pharmaceutical carrier or diluent. A suitable pharmaceutical form is a capsule.

In one group of compounds n is 3, A is trimethylene, $R_1$ is hydrogen or $(C_{1-5})$alkyl, $R_2$ is hydrogen or $(C_{1-5})$alkyl, $R_3$ is phenyl or benzyl unsubstituted or mono-, di- or trisubstituted independently by halogen, hydroxy, $(C_{1-4})$alkyl, $(C_{1-4})$alkoxy or di$(C_{1-4})$alkylamino; $(C_{3-6})$cycloalkyl; or an aromatic 5- or 6-membered heterocycle containing one heteroatom chosen from nitrogen, oxygen or sulphur, $R_4$ is hydrogen, chlorine, bromine or $(C_{1-4})$alkyl, $R_5$ is hydrogen, $(C_{1-4})$alkyl, $(C_{1-4})$alkoxy, or $(C_{1-4})$alkylthio, and X is —CO—.

In another group of compounds n is 2, either A is trimethylene and $R_1$ is hydrogen or $(C_{1-5})$alkyl, or A together with $R_1$ and the nitrogen atom to which $R_1$ is bound form a 4-piperidyl radical, and $R_2$ is hydrogen or $(C_{1-5})$alkyl, $R_3$ is $(C_{1-4})$alkyl; phenyl unsubstituted or mono-, di- or trisubstituted independently by halogen, $(C_{1-4})$alkyl or $(C_{1-4})$alkoxy; $(C_{3-6})$cycloalkyl; or an aromatic 5- or 6-membered heterocycle containing one heteroatom chosen from nitrogen, oxygen or sulphur, $R_4$ is hydrogen, chlorine, bromine or $(C_{1-4})$alkyl, $R_5$ is hydrogen, $(C_{1-4})$alkyl or $(C_{1-4})$alkoxy, and X is —CO— or —CS.

In the above Grollmann rat test on administration of 30 mg/kg s.c. of some of the above compounds of formula I the following results have been obtained:

| Example | Blood pressure lowering after 6 hours |
| --- | --- |
| (1) | −40 mm/Hg |
| (ai) | −11 mm/Hg. |

In the above Goldblatt dog test on administration once a day over five days of same of the above compounds of formula I at 10 mg/kg p.o. the following results were obtained [the dogs being treated with 1 g DOCA (Percorten-M)]

| Example | Systolic Blood pressure lowering on 5th day after 7 hours |
| --- | --- |
| (1) | −23 mm/Hg |
| (ai) | −28 mm/Hg |

What we claim is:
1. A compound of the formula

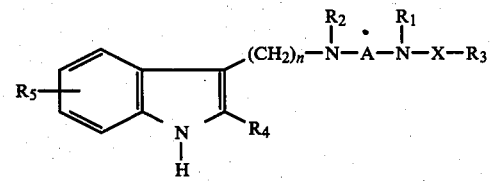

wherein
n is 2 or 3,
A is trimethylene optionally monosubstituted by $(C_{1-4})$alkyl, or 1,4-cyclohexylidene,
$R_1$ is hydrogen or $(C_{1-5})$alkyl,
$R_2$ is hydrogen or $(C_{1-5})$alkyl,
$R_3$ is unsubstituted phenyl,
$R_4$ is hydrogen,
$R_5$ is hydrogen, and
X is —CO—,
in free base form and in pharmaceutically acceptable salt form.

2. A compound according to claim 1 wherein
A is trimethylene or trimethylene substituted by alkyl in the middle carbon atom,
$R_1$ is methyl, and
$R_2$ is methyl.

3. A compound of claim 1 where n, $R_1$, A, $R_2$, $R_3$, $R_4$ and $R_5$, respectively, represent 2,

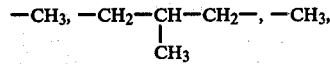

phenyl, H and H.

4. A compound of claim 1 wherein n=2, $R_1$ is methyl, A is —CH$_2$—CH(CH$_3$)—CH$_2$—, $R_2$ represents methyl, $R_3$ represents phenyl, and $R_4$ and $R_5$ both represent hydrogen, x represents —CO— in free base form or in pharmaceutically accetable salt form.

5. A compound of claim 1 which is N-benzoyl-N'-[3-(3-indolyl)propyl]-N'-methyl-1,3-diaminopropane.

* * * * *